United States Patent [19]

Matsuda et al.

[11] Patent Number: 4,810,812
[45] Date of Patent: Mar. 7, 1989

[54] THIOLCARBOXYLIC ACID ESTERS

[75] Inventors: Tatsuhito Matsuda, Kobe; Yasuaki Funae; Masahiro Yoshida, both of Suita; Tsuguo Takaya, Ohtsu, all of Japan

[73] Assignee: Nippon Shokubai Kagaku Kogyo Co., Ltd., Osaka, Japan

[21] Appl. No.: 135,045

[22] Filed: Dec. 18, 1987

[30] Foreign Application Priority Data

Dec. 26, 1986 [JP] Japan .................. 61-308337
Jul. 28, 1987 [JP] Japan .................. 62-186572
Oct. 22, 1987 [JP] Japan .................. 62-265440

[51] Int. Cl.$^4$ .................. C07C 153/023
[52] U.S. Cl. .................. 558/251
[58] Field of Search .................. 558/251

[56] References Cited

U.S. PATENT DOCUMENTS 2,378,535 6/1945 Brubaker .................. 558/251
4,606,864 8/1986 Warren .................. 558/251

FOREIGN PATENT DOCUMENTS 2093843 9/1982 United Kingdom .................. 558/251

OTHER PUBLICATIONS

Beilstein, E IV, 2458 (1960).
Chem. Abstracts, vol. 104 (1986), 104:50541p.
Beilstein, E IV, 5972 (1979).
J. Chem. Soc., 1894 (1948).
Beilstein, F (III), 2436 (1960).
J. Org. Chem., 33 (3), 1275 (1968).
J. Org. Chem., 26, 1995 (1961).

Primary Examiner—Mary C. Lee
Assistant Examiner—Robert C. Whittenbaugh
Attorney, Agent, or Firm—Sherman and Shalloway

[57] ABSTRACT

Thiolcarboxylic acid esters represented by the general formula

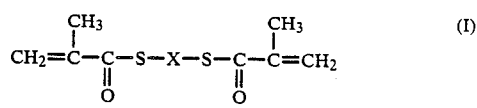

wherein X represents —CH$_2$CH$_2$—, $+$CH$_2$CH$_2$O$)_n$CH$_2$CH$_2$—, $+$CH$_2$CH$_2$S$)_m$—CH$_2$CH$_2$—, or

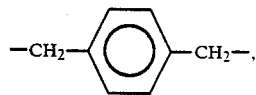

and n and m represent an integer of 1 to 3.

5 Claims, 15 Drawing Sheets

THIOLCARBOXYLIC ACID ESTERS

This invention relates to novel thiolcarboxylic acid esters useful as a material for optical plastics.

In recent years, transparent synthetic resins having a high refractive index have found increasing applications as optical plastic materials replacing inorganic optical materials because of their light weight and good impact strength, moldability or processability and dyeability.

A diethylene glycol bis-allyl carbonate resin as one example of conventional optical plastic materials has a refractive index of as low as 1.49 to 1.50. Hence, an eyeglass lens, for example, formed from this resin has the defect of being large in the thickness of both its center and edge as compared with inorganic optical lenses.

It is an object of this invention therefore to remedy the defects of conventional optical plastic materials, and to provide monomers which can give resins having a high refractive index and excellent transparency useful as an optical plastic material.

The present inventors, after conducting extensive work, have found that the above object is achieved by a compound (monomer) represented by the general formula (I)

wherein X represents —CH$_2$CH$_2$—,

$\{\text{CH}_2\text{CH}_2\text{O}\}_n\text{CH}_2\text{CH}_2$—, $\{\text{CH}_2\text{CH}_2\text{S}\}_m$—CH$_2$CH$_2$—, or and n and m represent an integer of 1 to 3.

Thus, according to this invention, the following eight compounds are provided.

Compound (1)

Compound (2)

Compound (3)

Compound (4)

Compound (5)

Compound (6)

Compound (7)

Compound (8)

Compounds (1) to (8) in accordance with this invention can be produced by reacting a dithiol derivative with a methacrylic acid derivative in accordance with the following formula.

In the formula, X is as defined above, and Y represents Cl, Br, OH, or an alkoxy group having 1 to 4 carbon atoms.

By polymerizing the novel thiolcarboxylic acid esters (1) to (8) represented by general formula (I) or copolymerizing them together with various compounds having olefinic double bonds, polymers or oligomers can be obtained. The polymers have a high refractive index and excellent transparency. In addition, since they are three-dimensionally crosslinked resins, they have good processability characteristics such as machinability and grindability, and are suitable as optical plastics.

The present invention will be specifically described with reference to the following Examples and the accompanying drawings.

In the accompanying drawings.

EXAMPLE 1

A 2000 ml glass flask equipped with a stirrer, a thermometer, a condenser and dropping funnels was charged with 5.36 g of trioctylmethyl ammonium chloride, 0.31 g of methoquinone and 480 g of chloroform. While the temperature of the inside of the flask was maintained at less than 10° C., a separately prepared mixture of 25.0 g of 1,2-dimercaptoethane and 700.8 g of a 7.5% by weight aqueous solution of potassium hydroxide and 66.6 g of methacryloyl chloride were added dropwise over 20 minutes through separate dropping funnels. After the addition, the mixture was further stirred at the same temperature for 15 minutes, and the reaction solution was then separated into two layers. The chloroform layer was washed with a 5% by weight aqueous solution of potassium hydroxide and then with water, and dried over anhydrous sodium sulfate. Chloroform was evaporated to give 52.6 g (yield 86.1%) of compound (1) of the following formula.

Figure 1:
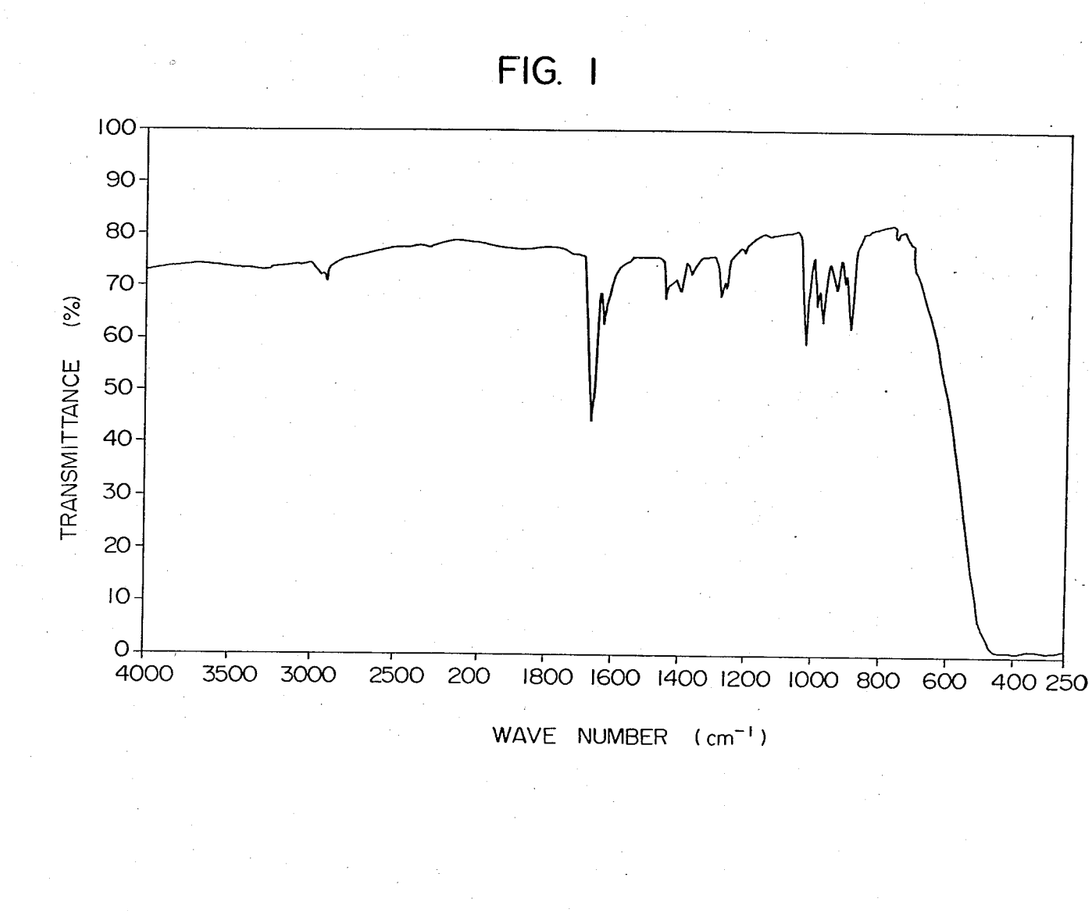
FIGS. 1, 4, 7, 10 and 13 are infrared absorption spectral charts of compounds (1), (2), (3), (5) and (8) respectively.
Figure 2:
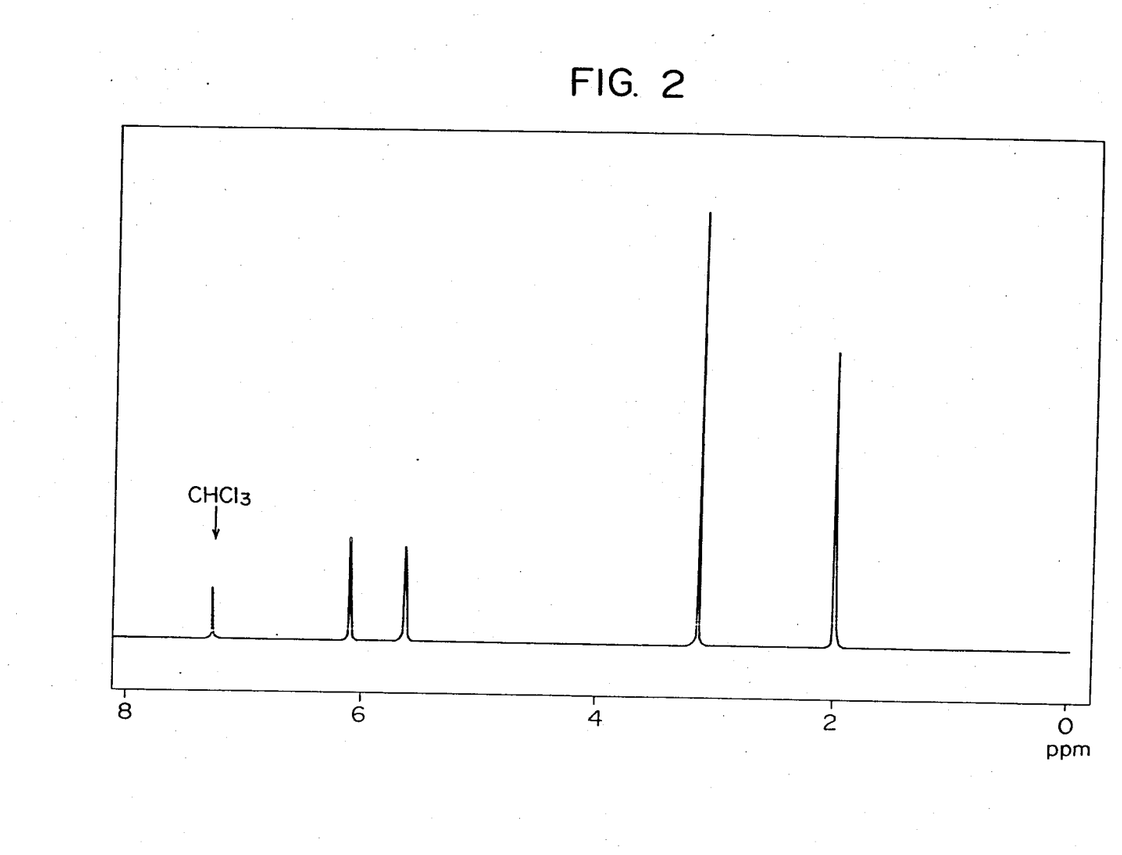
FIGS. 2, 5, 8, 11 and 14 are $^1$H-NMR spectral charts of compounds (1), (2), (3), (5) and (8) respectively.
Figure 3:
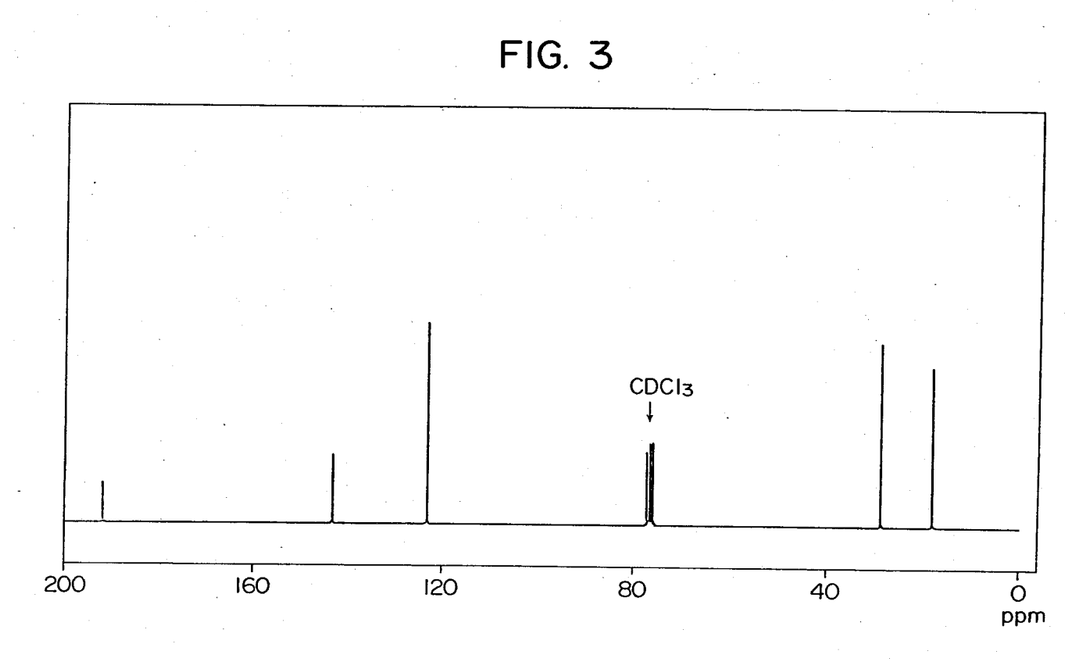
FIGS. 3, 6, 9, 12 and 15 are $^{13}$C-NMR spectral charts of compounds (1), (2), (3), (5) and (8).

The product was purified by distillation under reduced pressure, and its structure was determined by elemental analysis, mass analysis, and infrared absorption spectroscopy. The results are shown in Table 1. Its infrared absorption spectrum is shown in FIG. 1; its $^1$H-NMR spectrum, in FIG. 2; and its $^{13}$C-NMR spectrum, in FIG. 3.

EXAMPLE 2

By the same method as in Example 1, compound (2) of the following formula was prepared in a yield of 90.2% from 2-mercaptoethyl ether and methacryloyl chloride.

Figure 4:
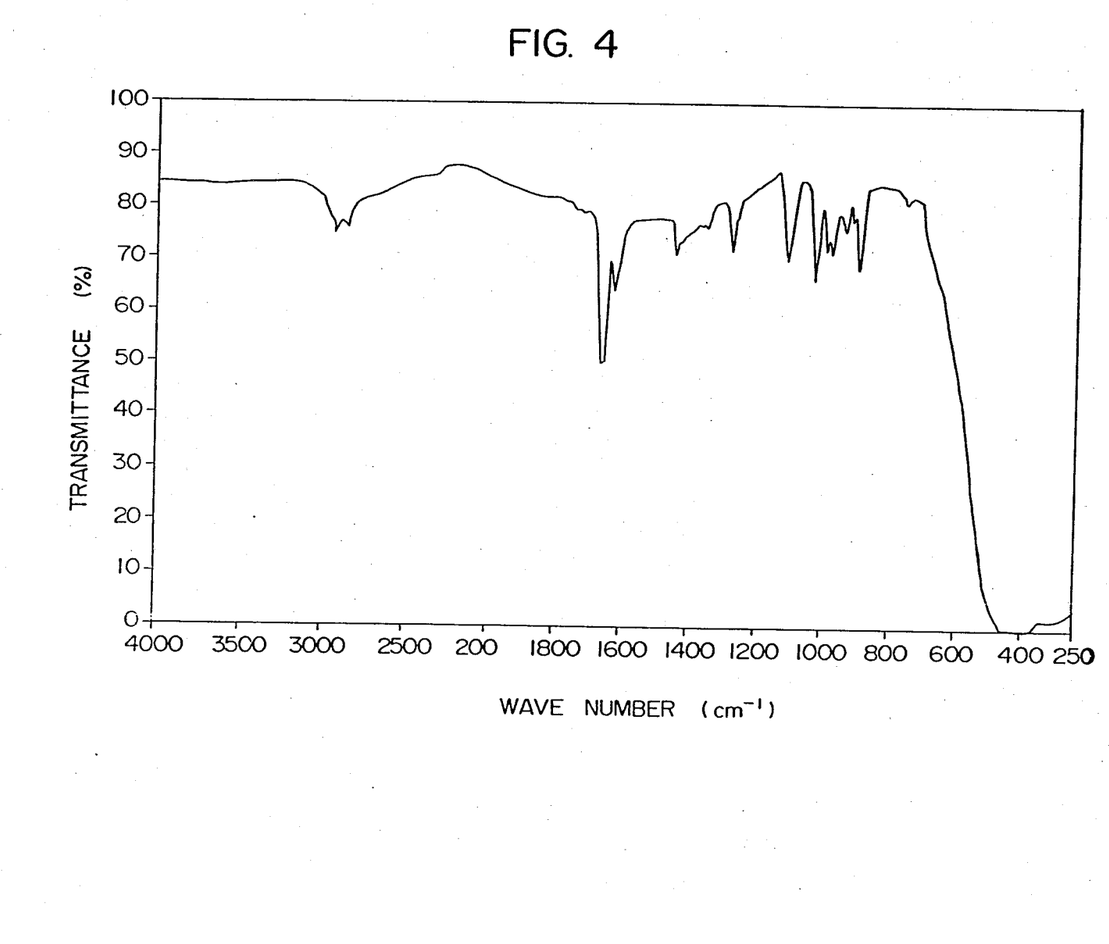
Figure 5:
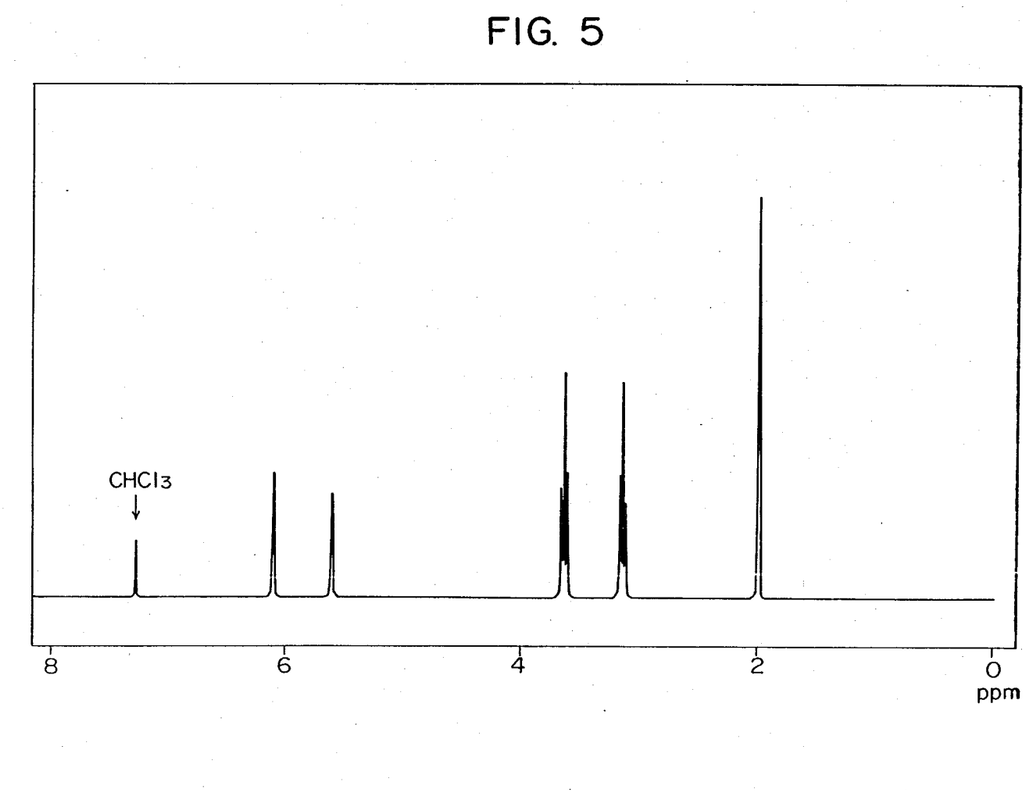
Figure 6:
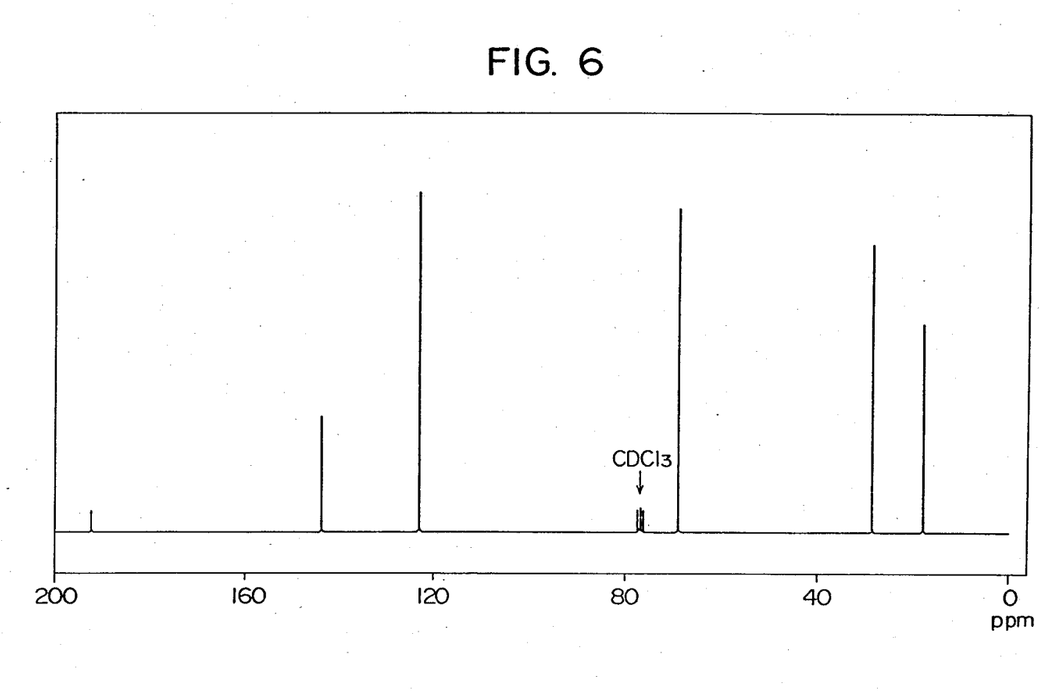

The product was purified by distillation under reduced pressure, and its structure was determined by elemental analysis, mass analysis, and infrared absorption spectroscopy. The results are shown in Table 1. Its infrared absorption spectrum is shown in FIG. 4; its $^1$H-NMR spectrum, in FIG. 5; and its $^{13}$C-NMR spectrum, in FIG. 6.

EXAMPLE 3

By the same method as in Example 1, compound (3) of the following formula was prepared in a yield of 89.3% from 1,2-bis-(2-mercaptoethoxy)ethane and methacryloyl chloride.

Figure 7:
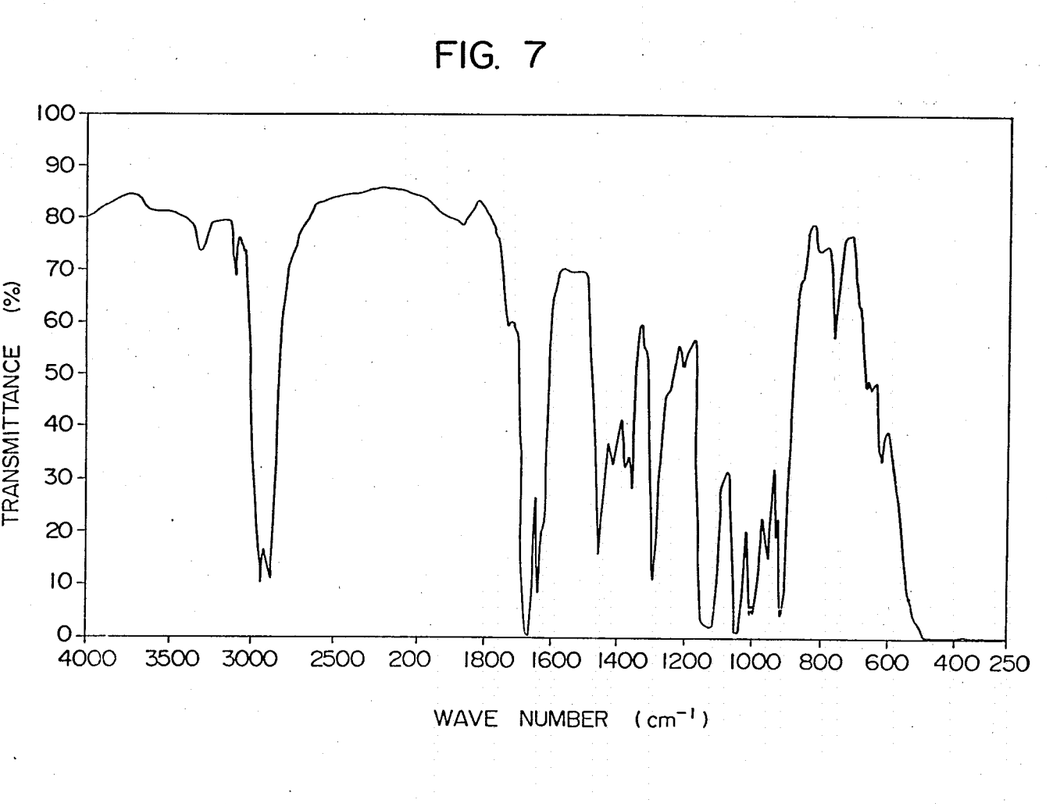
Figure 8:
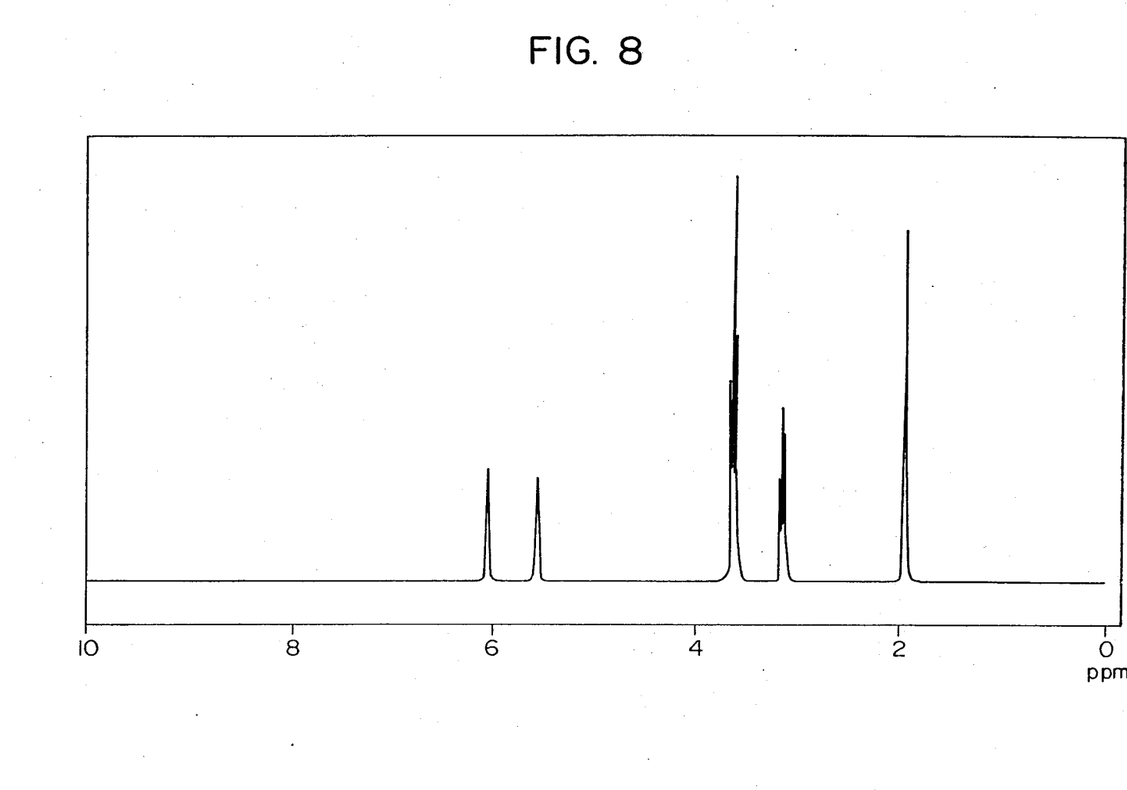
Figure 9:
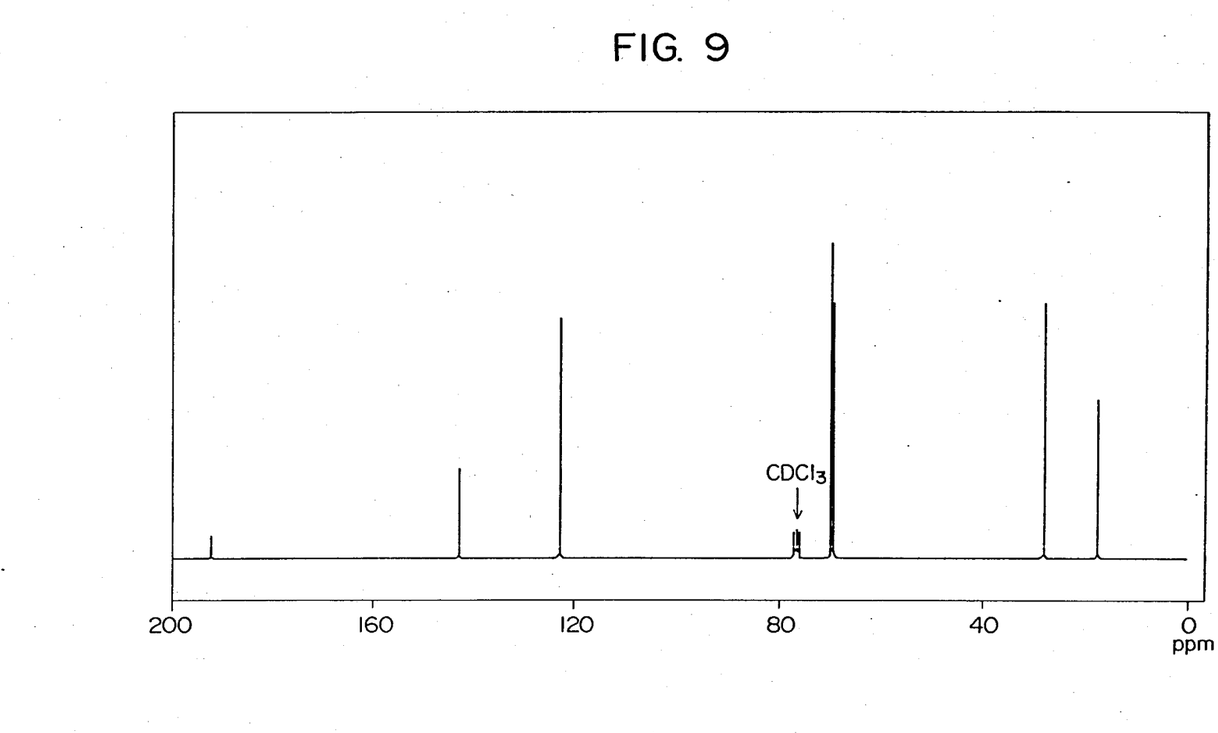

The product was purified by silica gel column chromatography, and its structure was determined by elemental analysis, mass analysis, and infrared absorption spectroscopy. The results are shown in Table 1. Its infrared absorption spectrum is shown in FIG. 7; its $^1$H-NMR spectrum, in FIG. 8; and its $^{13}$C-NMR spectrum, in FIG. 9.

EXAMPLE 4

By the same method as in Example 1, compound (4) of the following formula was prepared in a yield of 84.0% from bis-2-(2-mercaptoethoxy)ethyl ether and methacryloyl chloride.

The product was purified by silica gel column chromatography, and its structure was determined by elemental analysis, mass analysis, and infrared absorption spectroscopy. The results are shown in Table 1.

EXAMPLE 5

By the same method as in Example 1, compound (5) of the following formula was prepared in a yield of 93.1% from 2-mercaptoethyl sulfide and methacryloyl chloride.

Figure 10:
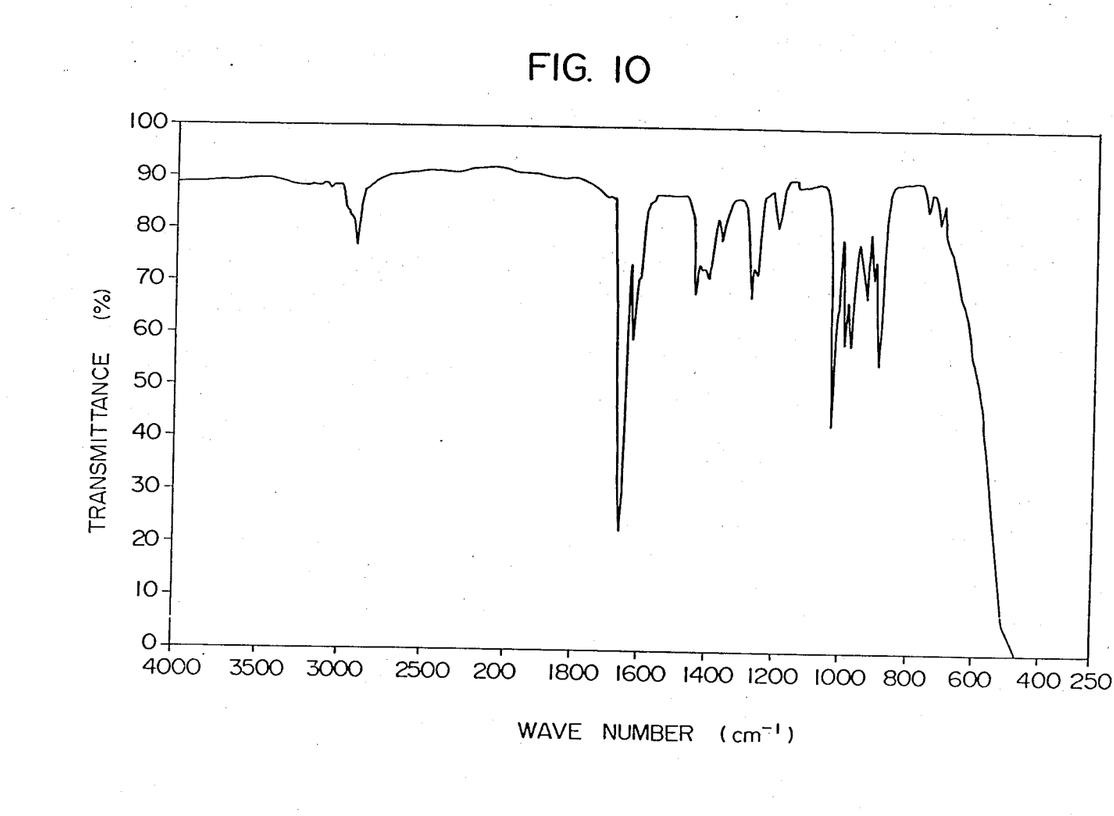
Figure 11:
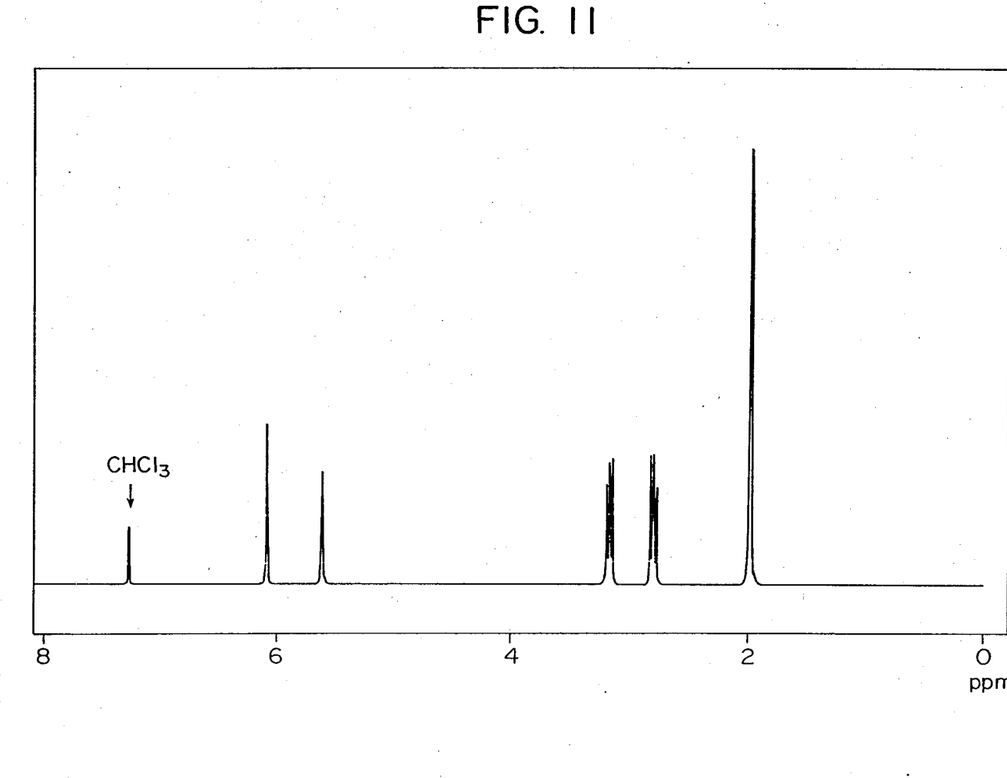
Figure 12:
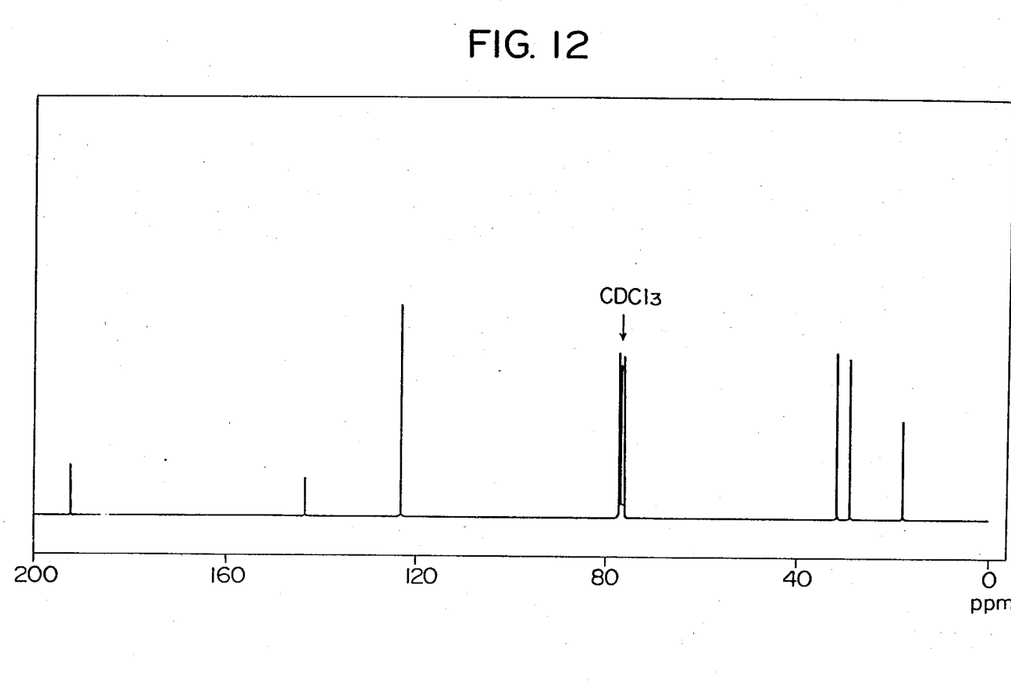

The product was purified by distillation under reduced pressure, and its structure was determined by elemental analysis, mass analysis, and infrared absorption spectroscopy. The results are shown in Table 1. Its infrared absorption spectrum is shown in FIG. 10; its $^1$H-NMR spectrum, in FIG. 11; and its $^{13}$C-NMR spectrum, in FIG. 12.

EXAMPLE 6

By the same method as in Example 1, compound (6) of the following formula was prepared in a yield of 88.7% from 1,2-bis-(2-mercaptoethylthio)ethane and methacryloyl chloride.

The product was purified by silica gel column chromatography, and its structure was determined by elemental analysis, mass analysis, and infrared absorption spectroscopy. The results are shown in Table 1.

EXAMPLE 7

By the same method as in Example 1, compound (7) of the following formula was prepared in a yield of 82.5% from bis-2-(2-mercaptoethylthio)ethyl sulfide and methacryloyl chloride.

The product was purified by silica gel column chromatography, and its structure was determined by elemental analysis, mass analysis, and infrared absorption spectroscopy. The results are shown in Table 1.

EXAMPLE 8

By the same method as in Example 1, compound (8) of the following formula was prepared in a yield of 73.6% from 1,4-bis-mercaptomethylbenzene and methacryloyl chloride.

Figure 13:
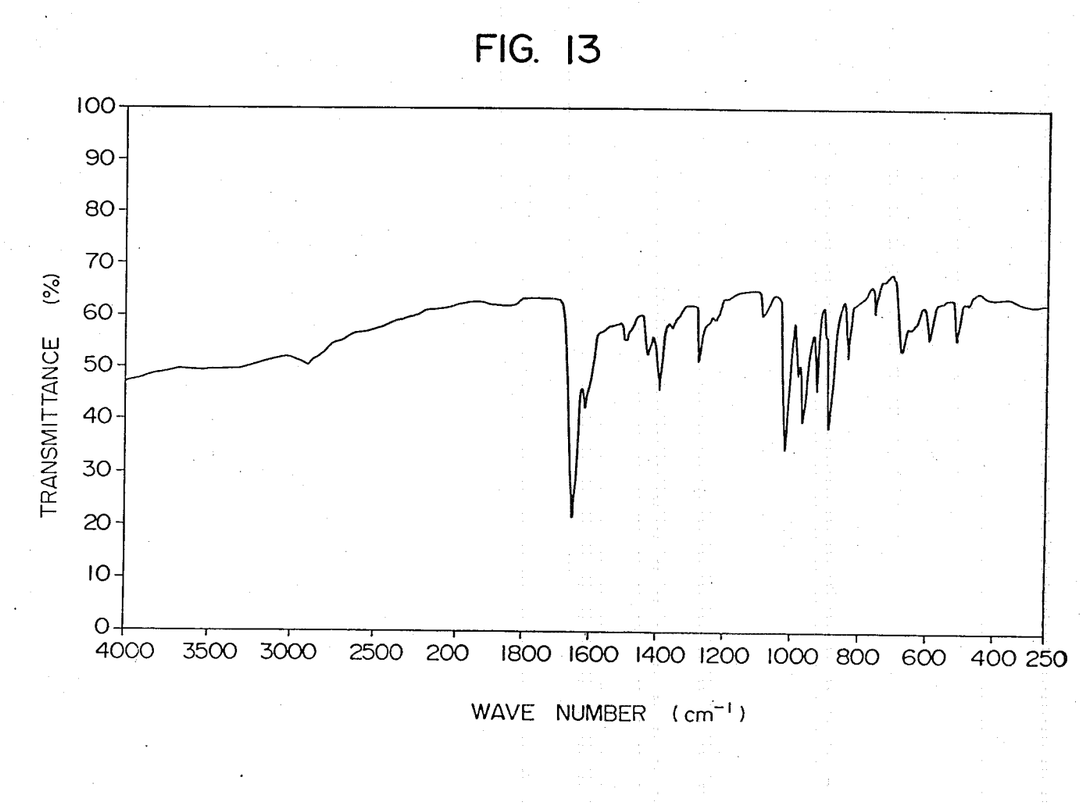
Figure 14:
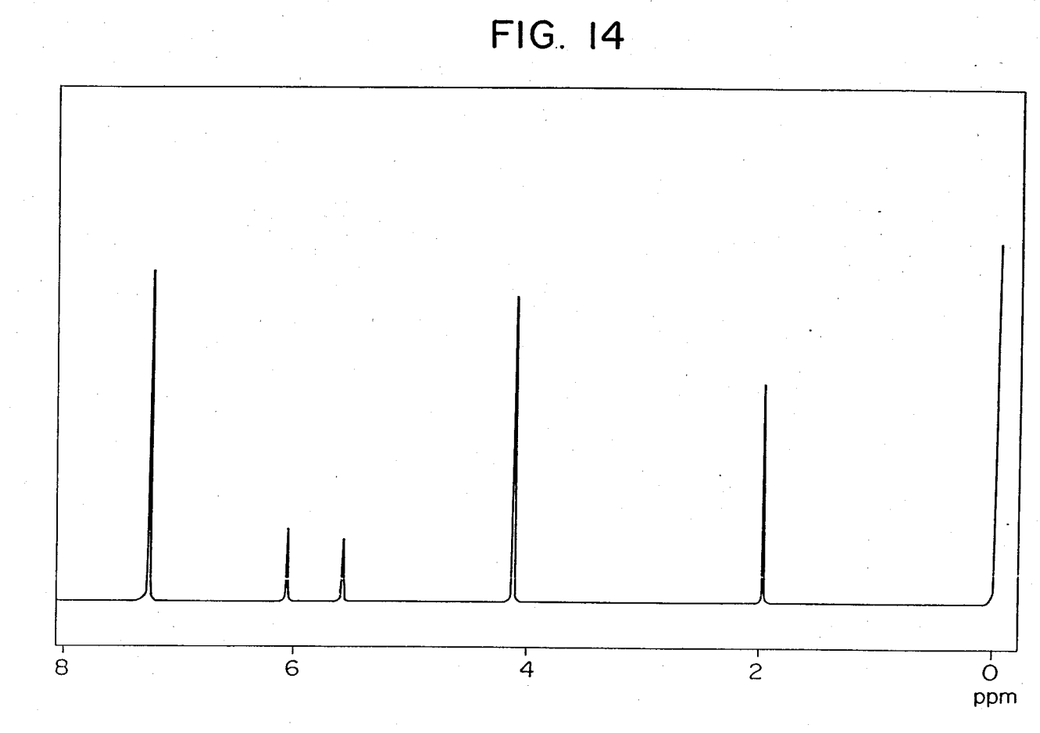
Figure 15:
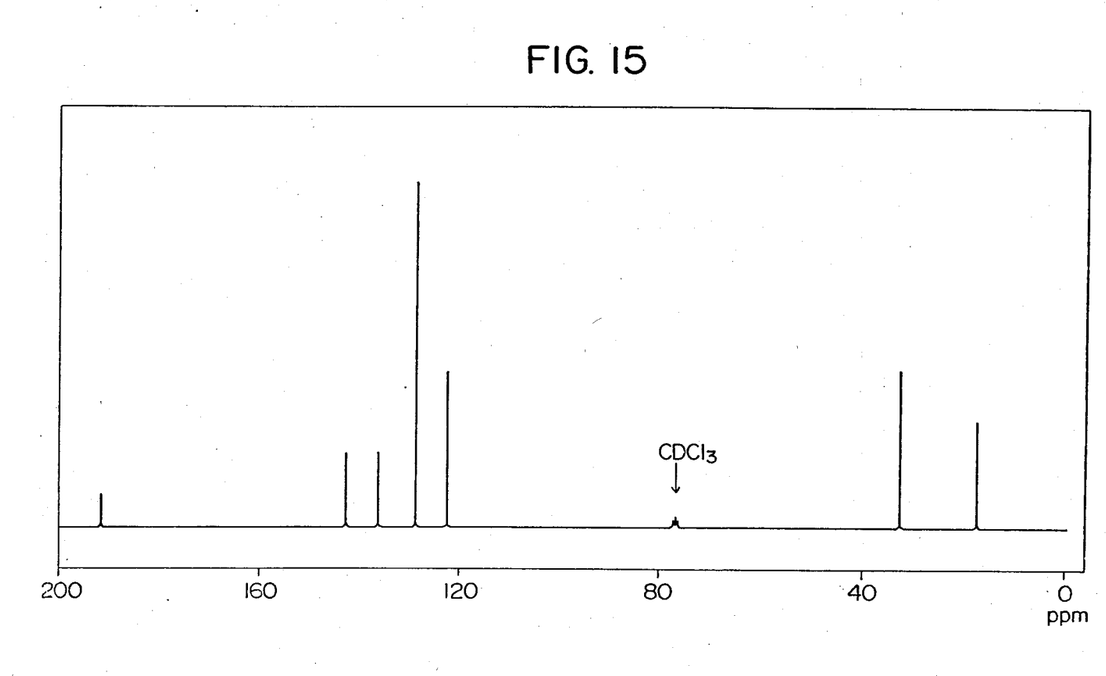

The product was purified by recrystallization, and its structure was determined by elemental analysis, mass analysis and infrared absortpion spectroscopy. The results are shown in Table 1. Its infrared absorption spectrum is shown in FIG. 13; its $^1$H-NMR spectrum, in FIG. 14; and its $^{13}$C-NMR spectrum, in FIG. 15.

TABLE 1

| Compound | Properties (boiling point) | Elemental analysis (%) Calculated | Found | Mass analysis (M$^+$) | Characteristic infrared absorption (cm$^{-1}$) |
|---|---|---|---|---|---|
| (1) | Colorless transparent liquid (124–125° C./1.1 mmHg) | C: 52.14 H: 6.13 S: 27.84 | C: 52.39 H: 6.09 S: 27.57 | 230 | $\nu_{C=O}$ 1660 |
| (2) | Colorless transparent liquid (133–134° C./1.0 mmHg) | C: 52.53 H: 6.61 S: 23.37 | C: 52.36 H: 6.72 S: 23.49 | 274 | $\nu_{C=O}$ 1660 |
| (3) | Colorless transparent liquid | C: 52.80 H: 6.96 S: 20.14 | C: 53.51 H: 7.04 S: 20.12 | 318 | $\nu_{C=O}$ 1660 |
| (4) | Colorless transparent liquid | C: 53.01 H: 7.23 S: 17.69 | C: 52.14 H: 7.09 S: 17.51 | 362 | $\nu_{C=O}$ 1660 |
| (5) | Colorless transparent liquid (170–171° C./1.0 mmHg) | C: 49.62 H: 6.25 S: 33.11 | C: 49.40 H: 6.38 S: 33.37 | 290 | $\nu_{C=O}$ 1660 |
| (6) | Colorless transparent liquid | C: 47.97 H: 6.33 S: 36.58 | C: 47.20 H: 6.46 S: 36.99 | 350 | $\nu_{C=O}$ 1660 |
| (7) | Colorless transparent liquid | C: 46.79 H: 6.38 S: 39.03 | C: 47.00 H: 6.49 S: 38.85 | 410 | $\nu_{C=O}$ 1660 |
| (8) | White crystals (melting point: 64–65° C.) | C: 62.71 H: 5.92 S: 20.93 | C: 62.63 H: 5.75 S: 21.01 | 306 | $\nu_{C=O}$ 1655 |

What is claimed is:

1. A thiolcarboxylic acid ester represented by the formula (I)

wherein X represents —CH$_2$CH$_2$—, $+$CH$_2$CH$_2$O$)_n$CH$_2$CH$_2$—, $+$CH$_2$CH$_2$S$)_m$—CH$_2$CH$_2$—, or and n and m represent an integer of 1 to 3.

2. The thiolcarboxylic acid ester of claim 1 wherein X is —CH$_2$CH$_2$—.

3. The thiolcarboxylic acid ester of claim 1 wherein X is $+$CH$_2$CH$_2$O)CH$_2$CH$_2+$ and n is an integer of 1 to 3.

4. The thiolcarboxylic acid ester of claim 1 wherein X is (CH$_2$CH$_2$S$+_m$CH$_2$CH$_2+$, and m is an integer of 1 to 3.

5. The thiolcarboxylic acid ester of claim 1 wherein X is

* * * * *

UNITED STATES PATENT AND TRADEMARK OFFICE
CERTIFICATE OF CORRECTION

PATENT NO. : 4,810,812
DATED : March 7, 1989
INVENTOR(S) : TATSUHITO MATSUDA ET AL.

It is certified that error appears in the above-identified patent and that said Letters Patent is hereby corrected as shown below:

Claim 3, line 2 of the claim, "$\{CH_2CH_2O)CH_2CH_2\}$" should read -- $\{CH_2CH_2O\}_n CH_2CH_2$- --.

Claim 4, line 2 of the claim, "$(CH_2CH_2S\{_m CH_2CH_2\}$" should read -- $\{CH_2CH_2S\}_m CH_2CH_2$- --.

Signed and Sealed this

Twenty-ninth Day of August, 1989

Attest:

DONALD J. QUIGG

Attesting Officer

Commissioner of Patents and Trademarks